United States Patent
Schertiger et al.

(10) Patent No.: US 11,998,705 B2
(45) Date of Patent: *Jun. 4, 2024

(54) URINARY CATHETER ASSEMBLY HAVING A URINARY CATHETER SEALED INSIDE OF A CLOSED PACKAGE

(71) Applicant: Coloplast A/S, Humlebaek (DK)

(72) Inventors: Lars Olav Schertiger, Fredensborg (DK); Chaabane Bougherara, Frederiksberg C (DK)

(73) Assignee: Coloplast A/S, Humlebaek (DK)

( * ) Notice: Subject to any disclaimer, the term of this patent is extended or adjusted under 35 U.S.C. 154(b) by 335 days.

This patent is subject to a terminal disclaimer.

(21) Appl. No.: 17/494,853

(22) Filed: Oct. 6, 2021

(65) Prior Publication Data

US 2022/0023585 A1     Jan. 27, 2022

Related U.S. Application Data

(63) Continuation of application No. 16/336,915, filed as application No. PCT/DK2017/050307 on Sep. 26, 2017, now Pat. No. 11,167,107.

(30) Foreign Application Priority Data

Sep. 27, 2016   (DK) .......................... PA 2016 70759

(51) Int. Cl.
*A61M 25/00*      (2006.01)
*A61M 25/01*      (2006.01)

(52) U.S. Cl.
CPC ...... *A61M 25/002* (2013.01); *A61M 25/0017* (2013.01); *A61M 25/0111* (2013.01);
(Continued)

(58) Field of Classification Search
CPC ............ A61M 25/002; A61M 25/0017; A61M 25/0111; A61M 2202/0496;
(Continued)

(56) References Cited

U.S. PATENT DOCUMENTS 761,235 A    5/1904   Kepler
1,060,665 A   5/1913   Bell
(Continued)

FOREIGN PATENT DOCUMENTS

CN    1106744 A    8/1995
CN    2347608 Y    11/1999
(Continued)

OTHER PUBLICATIONS

Hanafy el al., "Ancient Egyptian Medicine", Urology, vol. IV, No. 1, 1974, pp. 114-120.
(Continued)

*Primary Examiner* — Adam Marcetich
(74) *Attorney, Agent, or Firm* — Coloplast Corp., Coloplast A/S; Nick Baumann

(57) ABSTRACT

A urinary catheter assembly includes a urinary catheter sealed inside of a closed package. The urinary catheter has a first closure sealing a proximal opening and including a first extension portion that is coupled to the closed package, and a second closure sealing a distal opening and including a second extension portion coupled to the closed package.

13 Claims, 3 Drawing Sheets

(52) U.S. Cl.
CPC .............. *A61M 2025/0018* (2013.01); *A61M 2210/1089* (2013.01)

(58) Field of Classification Search
CPC ...... A61M 2209/06; A61M 2025/0175; A61M 25/01; A61M 2210/1085; A61M 2210/1089; A61M 25/0009; A61M 25/0136; B65D 77/30; B65D 25/087; B65D 2575/362; B65D 2577/205; B65D 5/70; B65D 51/00; B65D 51/2864; B65D 51/2878; B65D 65/38; B65D 75/30
See application file for complete search history.

(56) References Cited

U.S. PATENT DOCUMENTS

| | | | |
|---|---|---|---|
| 1,120,549 | A | 12/1914 | Schellberg |
| 2,856,932 | A | 10/1958 | Griffitts |
| 3,154,080 | A | 10/1964 | Rowan et al. |
| 3,321,097 | A | 5/1967 | Solowey |
| 3,421,509 | A | 1/1969 | Fiore |
| 3,444,860 | A | 5/1969 | Harrell |
| 3,648,704 | A | 3/1972 | Jackson |
| 3,683,928 | A | 8/1972 | Kuntz |
| 3,750,875 | A | 8/1973 | Juster |
| 3,762,399 | A | 10/1973 | Riedell |
| 3,794,042 | A | 2/1974 | Holmes et al. |
| 3,854,483 | A | 12/1974 | Powers |
| 3,894,540 | A | 7/1975 | Bonner, Jr. |
| 3,930,580 | A | 1/1976 | Bazell et al. |
| 3,934,721 | A | 1/1976 | Juster et al. |
| 3,967,728 | A | 7/1976 | Gordon et al. |
| 4,026,296 | A | 5/1977 | Stoy et al. |
| 4,062,363 | A | 12/1977 | Bonner, Jr. |
| 4,140,127 | A | 2/1979 | Cianci et al. |
| 4,168,699 | A | 9/1979 | Hauser |
| 4,170,996 | A | 10/1979 | Wu |
| 4,652,259 | A | 3/1987 | O'Neil |
| 4,692,154 | A | 9/1987 | Singery et al. |
| 4,875,719 | A | 10/1989 | Mylett |
| 5,226,530 | A | 7/1993 | Golden |
| 5,454,798 | A | 10/1995 | Kubalak et al. |
| 5,645,048 | A | 7/1997 | Brodsky et al. |
| 5,688,459 | A | 11/1997 | Mao et al. |
| 5,895,374 | A | 4/1999 | Roedsten |
| 6,045,542 | A | 4/2000 | Cawood |
| 6,059,107 | A | 5/2000 | Noested et al. |
| 6,065,597 | A | 5/2000 | Pettersson et al. |
| 6,073,759 | A | 6/2000 | Lamborne et al. |
| 6,090,075 | A | 7/2000 | House |
| 6,117,120 | A | 9/2000 | Heininger |
| 6,391,010 | B1 | 5/2002 | Wilcox |
| 6,402,726 | B1 | 6/2002 | Genese |
| 6,544,240 | B1 | 4/2003 | Borodulin et al. |
| 6,578,709 | B1 | 6/2003 | Kavanagh et al. |
| 6,602,244 | B2 | 8/2003 | Kavanagh et al. |
| 6,634,498 | B2 | 10/2003 | Kayeroed et al. |
| 6,899,355 | B2 | 5/2005 | Klein et al. |
| 6,986,868 | B2 | 1/2006 | Madsen |
| 7,311,698 | B2 | 12/2007 | Tanghoj et al. |
| 7,380,658 | B2 | 6/2008 | Murray et al. |
| 7,886,907 | B2 | 2/2011 | Murray et al. |
| 8,011,505 | B2 | 9/2011 | Murray et al. |
| 8,205,745 | B2 | 6/2012 | Murray et al. |
| 8,523,843 | B2 | 9/2013 | Kavanagh et al. |
| 8,720,685 | B2 | 5/2014 | Murray et al. |
| 8,740,863 | B2 | 6/2014 | Nestenborg et al. |
| 9,028,858 | B2 | 5/2015 | Nielsen et al. |
| 9,072,862 | B2 | 7/2015 | Murray et al. |
| RE47,513 | E | 7/2019 | Murray et al. |
| 10,758,704 | B2 | 9/2020 | Hickmott et al. |
| 2001/0001443 | A1 | 5/2001 | Kayerod et al. |
| 2002/0144920 | A1 | 10/2002 | Samuels |
| 2002/0151834 | A1 | 10/2002 | Utterberg |
| 2002/0193762 | A1 | 12/2002 | Suydam |
| 2003/0060807 | A1 | 3/2003 | Tanghoj et al. |
| 2005/0015076 | A1 | 1/2005 | Giebmeyer et al. |
| 2005/0061698 | A1 | 3/2005 | Delaney et al. |
| 2005/0070882 | A1 | 3/2005 | McBride |
| 2005/0107860 | A1 | 5/2005 | Ignagni et al. |
| 2005/0261664 | A1 | 11/2005 | Rome et al. |
| 2006/0025753 | A1 | 2/2006 | Kubalak et al. |
| 2006/0111681 | A1 | 5/2006 | Vernon |
| 2006/0142737 | A1 | 6/2006 | Tanghoj |
| 2006/0161115 | A1 | 7/2006 | Fangrow |
| 2006/0196783 | A1 | 9/2006 | Bruun et al. |
| 2007/0225687 | A1 | 9/2007 | House |
| 2007/0289887 | A1* | 12/2007 | Murray .................. B65D 51/00 53/396 |
| 2008/0171992 | A1 | 7/2008 | House |
| 2008/0172016 | A1 | 7/2008 | House |
| 2008/0260576 | A1* | 10/2008 | Bruun ................ A61M 25/0111 206/364 |
| 2009/0208368 | A1 | 8/2009 | Waldrep et al. |
| 2011/0114520 | A1 | 5/2011 | Matthison-Hansen |
| 2011/0120892 | A1 | 5/2011 | Frederiksen et al. |
| 2011/0160662 | A1 | 6/2011 | Stout et al. |
| 2011/0160704 | A1 | 6/2011 | Park |
| 2011/0172491 | A1 | 7/2011 | Piskun et al. |
| 2011/0230864 | A1 | 9/2011 | House |
| 2011/0251572 | A1 | 10/2011 | Nishtala et al. |
| 2011/0295239 | A1 | 12/2011 | Gustavsson |
| 2012/0165790 | A1 | 6/2012 | Gustavsson et al. |
| 2012/0271282 | A1 | 10/2012 | Schertiger et al. |
| 2012/0316515 | A1 | 12/2012 | Terry |
| 2013/0161208 | A1 | 6/2013 | Gustavsson |
| 2013/0165867 | A1 | 6/2013 | Isaacson et al. |
| 2013/0186778 | A1 | 7/2013 | Terry |
| 2013/0261607 | A1 | 10/2013 | Nielsen |
| 2013/0261608 | A1 | 10/2013 | Tanghoej |
| 2013/0292286 | A1 | 11/2013 | Van et al. |
| 2013/0327664 | A1 | 12/2013 | Tanghoej |
| 2013/0338615 | A1 | 12/2013 | Zeller |
| 2014/0194842 | A1 | 7/2014 | Schertiger et al. |
| 2014/0262859 | A1 | 9/2014 | Knapp et al. |
| 2015/0068927 | A1 | 3/2015 | McBurney et al. |
| 2015/0112314 | A1 | 4/2015 | Gustavsson et al. |
| 2015/0133898 | A1 | 5/2015 | Murray et al. |
| 2015/0173937 | A1 | 6/2015 | Jackson |
| 2015/0202421 | A1 | 7/2015 | Ma et al. |
| 2015/0250656 | A1 | 9/2015 | Maksimow |
| 2015/0258305 | A1 | 9/2015 | Dye |
| 2015/0265801 | A1 | 9/2015 | Rostami |
| 2015/0306342 | A1 | 10/2015 | Rostami et al. |
| 2016/0015929 | A1 | 1/2016 | Tanghoej et al. |
| 2016/0038713 | A1 | 2/2016 | Kearns et al. |
| 2016/0038717 | A1 | 2/2016 | Murray et al. |
| 2016/0193447 | A1 | 7/2016 | Matthiassen |
| 2017/0000978 | A1 | 1/2017 | Murray et al. |
| 2017/0203910 | A1 | 7/2017 | Buse et al. |
| 2017/0216557 | A1 | 8/2017 | Kearns et al. |
| 2020/0222659 | A1 | 7/2020 | Schertiger et al. |
| 2021/0290895 | A1 | 9/2021 | Nielsen et al. |

FOREIGN PATENT DOCUMENTS

| | | |
|---|---|---|
| CN | 1718940 A | 1/2006 |
| CN | 1795024 A | 6/2006 |
| CN | 101132826 A | 2/2008 |
| CN | 101803968 A | 8/2010 |
| CN | 202173621 U | 3/2012 |
| CN | 102654224 A | 9/2012 |
| CN | 102892452 A | 1/2013 |
| CN | 103127597 A | 6/2013 |
| CN | 103301551 A | 9/2013 |
| CN | 103791132 A | 5/2014 |
| CN | 103945893 A | 7/2014 |
| CN | 104379210 A | 2/2015 |
| CN | 204840604 U | 12/2015 |
| DE | 2227416 A1 | 12/1972 |
| DE | 2458217 A1 | 6/1976 |
| DE | 10213411 A1 | 10/2003 |
| DE | 10334372 A1 | 2/2005 |
| DE | 102009031447 A1 | 1/2011 |

(56) References Cited

FOREIGN PATENT DOCUMENTS

| | | |
|---|---|---|
| EP | 0166998 A2 | 1/1986 |
| EP | 0217771 A1 | 4/1987 |
| EP | 0679506 A1 | 11/1995 |
| EP | 0923398 A1 | 6/1999 |
| EP | 1018323 A1 | 7/2000 |
| EP | 1312385 A1 | 5/2003 |
| EP | 2072075 A1 | 6/2009 |
| EP | 2423125 A1 | 2/2012 |
| EP | 2423126 A1 | 2/2012 |
| EP | 2423127 A1 | 2/2012 |
| EP | 2695636 A1 | 2/2014 |
| EP | 3210909 A1 | 8/2017 |
| EP | 3392167 A1 | 10/2018 |
| GB | 0322426 A | 12/1929 |
| GB | 2007507 A | 5/1979 |
| JP | 55-012265 A | 1/1980 |
| JP | 2001-139059 A | 5/2001 |
| JP | 2007-533331 A | 11/2007 |
| JP | 2009-279456 A | 12/2009 |
| JP | 2014023605 A | 2/2014 |
| JP | 5512265 B2 | 6/2014 |
| RU | 2012129843 A | 1/2014 |
| RU | 2013130998 A | 1/2015 |
| RU | 2013131785 A | 1/2015 |
| RU | 2584649 C2 | 5/2016 |
| RU | 2598811 C2 | 9/2016 |
| WO | 92/04932 A1 | 4/1992 |
| WO | 94/06377 A1 | 3/1994 |
| WO | 94/16747 A1 | 8/1994 |
| WO | 96/30277 A1 | 10/1996 |
| WO | 97/26937 A1 | 7/1997 |
| WO | 97/47349 A1 | 12/1997 |
| WO | 98/06642 A1 | 2/1998 |
| WO | 98/11932 A1 | 3/1998 |
| WO | 98/19729 A1 | 5/1998 |
| WO | 2000016843 A1 | 3/2000 |
| WO | 00/30575 A1 | 6/2000 |
| WO | 00/30696 A1 | 6/2000 |
| WO | 00/47494 A1 | 8/2000 |
| WO | 01/52763 A1 | 7/2001 |
| WO | 03/02178 A2 | 1/2003 |
| WO | 03/92779 A1 | 11/2003 |
| WO | 2004/050155 A1 | 6/2004 |
| WO | 2005/004964 A1 | 1/2005 |
| WO | 2005/004970 A1 | 1/2005 |
| WO | 2005/014055 A2 | 2/2005 |
| WO | 2007/022223 A2 | 2/2007 |
| WO | 2007/106431 A2 | 9/2007 |
| WO | 2007/146820 A2 | 12/2007 |
| WO | 2008/146836 A1 | 12/2008 |
| WO | 2009152609 A1 | 12/2009 |
| WO | 2010/006620 A1 | 1/2010 |
| WO | 2011/000353 A1 | 1/2011 |
| WO | 2011/079129 A1 | 6/2011 |
| WO | 2011/109393 A1 | 9/2011 |
| WO | 2012/016570 A2 | 2/2012 |
| WO | 2012/016571 A2 | 2/2012 |
| WO | 2013029620 A1 | 3/2013 |
| WO | 2013/049733 A2 | 4/2013 |
| WO | 2014/142917 A1 | 9/2014 |
| WO | 2015/142506 A1 | 9/2015 |
| WO | 2015/184365 A1 | 12/2015 |
| WO | 2016/206701 A1 | 12/2016 |
| WO | 2017/178030 A1 | 10/2017 |
| WO | 2018/059637 A1 | 4/2018 |
| WO | 2020/015804 A1 | 1/2020 |

OTHER PUBLICATIONS

Nacey et al. "The Evolution and Development of the Urinary Catheter", Aust. N.Z. J. Surg., 1993, vol. 63, pp. 815-819.

Sherman, "Medical Device Packaging Handbook", A Series of Reference Books, 1998, pp. 1-11.

* cited by examiner the URINARY CATHETER ASSEMBLY HAVING A URINARY CATHETER SEALED INSIDE OF A CLOSED PACKAGE

FIELD OF THE INVENTION

Present invention relates to relieving urinary retention and the field of intermittent catheterization.

BRIEF SUMMARY

Embodiments provide a urinary catheter assembly comprising an outer package of gas-impermeable material and an intermittent urinary catheter arranged inside the outer package. The catheter comprises a proximal insertion end, a distal connection end, and a connector at the distal end. The connector defines a distal opening. The catheter assembly further comprises a sleeve of liquid-impermeable material configured to define at least part of a liquid tight enclosure. The enclosure encloses the insertable part of the catheter. The enclosure is closed by a first closure in the proximal end and a second closure in the distal end. The second closure is configured to be opened as the outer package is opened and the first closure is configured to be opened as the catheter and sleeve is removed from the outer package. A method of removing the catheter from the outer package is also disclosed.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

DETAILED DESCRIPTION

Figure 1:
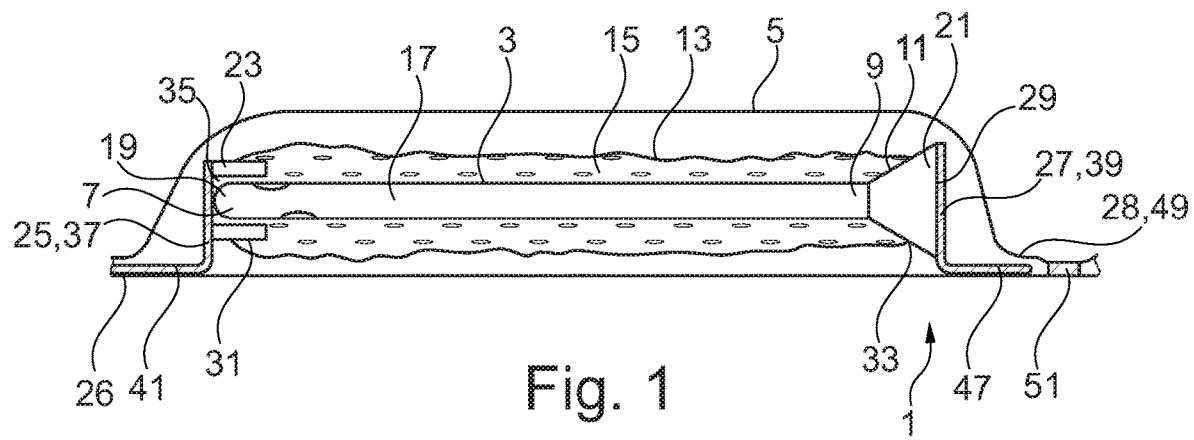
FIG. 1 illustrates a schematic cross-sectional side view of an embodiment of a catheter assembly.

Intermittent urinary catheter assemblies for draining the bladder are increasingly used for catheterization. Typically, urinary catheters are used by patients suffering from urinary incontinence or by disabled individuals like paraplegics or tetraplegics, who may have no control permitting voluntary urination and for whom catheterization may be the way of urinating.

Intermittent catheters are typically inserted by the user him- or herself and sits only in the urethra and bladder for as long as it takes to empty the bladder—e.g. for about 5-10 minutes. Intermittent catheters are used every 4-6 hours to empty the bladder corresponding roughly to the interval that people having no urinary problems will usually go to the bathroom. Intermittent catheters are typically relatively rigid since they have to be inserted by the user him-/herself and since they do not need to sit in the urethra for days or weeks. An important feature for the intermittent catheter is to ease the insertion into the urethra. This is done by providing the intermittent catheter with a low friction surface. Non-limiting examples of such are hydrophilic coated catheters which are subsequently wetted by a swelling media in order to produce a low friction surface, or oil or water based gel which is applied to the catheter before insertion into the urethra.

Intermittent urinary catheters may be provided with a hydrophilic coating that needs to be wetted prior to use and thereby absorbs a considerable amount of liquid. Such a hydrophilic coating will provide a very lubricious surface that has very low friction when the catheter is to be inserted. Hydrophilic coated catheters, where the coating absorbs a considerable amount of liquid for a low friction surface (swelling degree >100% of original thickness), will only be suitable for intermittent catheters, because the hydrophilic surface coating would stick inside the mucosa of the urethra if left inside the body for a longer period, due to the hydrophilic coating transforming from being highly lubricious when fully wetted to being adhesive when the hydration level of the coating is reduced.

Embodiments relate to intermittent catheters with a hydrophilic coating of the kind that is wetted prior to use to absorb an amount of liquid and to provide a lubricious surface.

In the following Detailed Description, reference is made to the accompanying drawings, which form a part hereof, and in which is shown by way of illustration specific embodiments in which the invention may be practiced. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments provide a urinary catheter assembly comprising an outer package of gas-impermeable material and an intermittent urinary catheter arranged inside the outer package, the catheter comprising a proximal insertion end, a distal connection end, and a connector at the distal end, the connector defining a distal opening, the catheter assembly further comprising a sleeve of liquid-impermeable material configured to define at least part of a liquid tight enclosure, the enclosure enclosing the insertable part of the catheter, the enclosure being closed by a first closure in the proximal end and a second closure in the distal end, the second closure being configured to be opened as the outer package is opened and the first closure being configured to be opened as the catheter and sleeve is removed from the outer package.

Embodiments provide a method of removing a catheter from a catheter assembly, the catheter assembly comprising an outer package of gas-impermeable material, an intermittent urinary catheter arranged inside the outer package, and a liquid tight enclosure enclosing an insertable part of the catheter and a liquid substance in the package, the liquid tight enclosure being closed by a first and a second closure and being at least partly defined by a sleeve in the outer package, the method comprising the steps of:

simultaneously opening the outer package and opening the second closure of the liquid tight enclosure; and
subsequently removing the catheter from the outer package, and using movement of the catheter relative to the outer package to simultaneously open the first closure of the liquid tight enclosure, and removing the catheter from the outer package along with the sleeve.

Embodiments provide a urinary catheter assembly comprising an outer package of gas-impermeable foil material and an intermittent urinary catheter arranged inside the outer package, the catheter comprising a proximal insertion end, a handle in the proximal end defining a proximal opening, a distal connection end, and a connector at the distal end, the connector defining a distal opening, the catheter assembly further comprising a sleeve of liquid-impermeable material defining a liquid tight enclosure, the enclosure enclosing the insertable part of the catheter, the enclosure being closed by a first closure in the proximal end and a second closure in the distal end, wherein the second closure comprises a peelable distal foil arranged to seal the distal opening of the connector, the distal foil being attached to the outer package at a distal end, and wherein the first closure comprises a peelable proximal foil arranged to seal the proximal opening of the handle, the proximal foil being attached to the outer package at a proximal end.

Embodiments provide a urinary catheter assembly comprising an outer package of gas-impermeable material and an intermittent urinary catheter arranged inside the outer package, the outer package comprising a substantially rigid structure and a lid at a distal end of the outer package, the catheter comprising a proximal insertion end, a handle in the proximal end defining a proximal opening, a distal connection end, and a connector at the distal end, the connector defining a distal opening, the catheter assembly further comprising a sleeve of liquid-impermeable material defining a liquid tight enclosure, the enclosure enclosing the insertable part of the catheter, the enclosure being closed by a first closure in the proximal end and a second closure in the distal end, wherein the second closure comprises a distal plug arranged to seal the distal opening of the connector, the distal plug being attached to the lid of the outer package, and wherein the first closure comprises a proximal plug arranged to seal the proximal opening of the handle, the proximal plug being attached to the outer package at a proximal end.

In present context, the insertable part of the catheter most often corresponds to the part of the catheter having a hydrophilic coating. In an embodiment, the sleeve covers at least half of the insertable part of the catheter. The length of the sleeve is long enough to allow the user to conveniently handle the catheter without accidentally touching the insertable part of the catheter. Also, the larger the part of the catheter that is covered by the sleeve, the more conveniently the user is allowed to handle the catheter without accidentally touching the insertable part of the catheter. During insertion, the sleeve is retractable towards the distal end of the catheter such that the sleeve allows the catheter to be inserted without the sleeve entering the urethra.

In embodiments, the sleeve covers at least three quarters of the insertable part of the catheter. The length of the sleeve is so long that it allows the user to conveniently handle the catheter without accidentally touching the insertable part of the catheter. In one embodiment, the sleeve covers the whole of the insertable part of the catheter when the sleeve protects the catheter. The sleeve may also be referred to as a protective sleeve. During insertion, the sleeve is retractable towards the distal end of the catheter such that the sleeve allows the catheter to be inserted without the sleeve entering the urethra.

In embodiments, the catheter assembly provides a ready-to-use urinary intermittent catheter with a sleeve providing reduced chance of contamination upon catheter insertion. In embodiments, the catheter is provided with the hydrophilic coating of the kind that requires wetting before insertion. The hydrophilic surface coating is not suitable for indwelling use, because the surface coating tends to stick inside the mucosa of the urethra if left inside the body for a period exceeding 5-20 minutes, due to the hydrophilic coating transforming from being highly lubricious when fully wetted (95% weight liquid) to being adhesive when the hydration level of the coating is reduced (<75% weight liquid).

In embodiments, the liquid tight enclosure is provided with an activating medium in the form of liquid for wetting the hydrophilic coating of the catheter. In one embodiment, the activating medium is a water based substance, such as sterile water, saline-solution, or any water based liquid. The liquid is then released from the liquid tight enclosure, preferably into the outer package, when the catheter is removed from the outer package providing a ready-to-use catheter with a sleeve being substantially dry to the touch.

In embodiments, the outer package is water vapour impermeable. By water vapour impermeable is meant that the outer package is able to keep the hydrophilic coating of the catheter fully hydrated for the storage time, which is up to 3 years. In an embodiment, the outer package is made as a foil package of laminated thermoplastic material comprising aluminium. Aluminium provides excellent water vapour impermeability. In one embodiment, the outer package is an injection-moulded hard box and may be made of high density polyethylene or high density polypropylene in a thickness of 0.7 mm or more.

In the following, whenever referring to a proximal end of an element of embodiments, the referral is to the end adapted for insertion. Whenever referring to the distal end of an element, the referral is to the end opposite the insertion end. In other words, the proximal end is the end closest to the user, when the catheter is to be inserted and the distal end is the opposite end—the end furthest away from the user when the catheter is to be inserted. The same definitions apply to the outer package and sleeve—the proximal end is the end storing the proximal end of the catheter and the distal end is the opposite end.

In one embodiment, the sleeve is configured to define the whole of the liquid tight enclosure. In this case, the sleeve is continuous and is arranged all around the catheter. Accordingly, the first and second closures form part of the sleeve. In one embodiment, the first and second closures then comprise e.g. a rupturable zone or a peelable weld of the sleeve. In one embodiment, the sleeve is configured to define only part of the liquid tight enclosure. In this case, other parts of the catheter or catheter assembly define the remaining part of the enclosure. In one embodiment, the sleeve is attached to the connector in the distal end and a handle in the proximal end, in which case the connector and handle form part of the enclosure. In this embodiment, each of the first and second closures form part of the sleeve or are configured to detachably close other parts of the catheter, such as an opening of the connector in the distal end or an opening of the handle in the proximal end. Accordingly, the first and second closures may comprise different types of structures and joints including peelable welds and rupturable zones. The closures may also comprise foils or plugs, a closed plug preferably being held in place by friction. The opening force of each closure depends on the structures and joints it comprises. This enables deliberate design of closures and associated opening forces.

The closures may be attached to the outer package by attachments or they may be integrally formed with the outer package. The attachments could also comprise different types of attachments including welds, and different kinds of adhesives, e.g. glue between the closure and the outer package, e.g. by use of a compound known in the art.

Usually, catheters used as urinary draining devices are from size 8 FR to size 18 FR. FR (or French size or Charriere (Ch)) is a standard gauge for catheters approximately corresponding to the outer circumference in mm. More accurately, the outer diameter of the catheter in mm corresponds to FR divided by 3. Thus 8 FR corresponds to a catheter with an outer diameter of 2.7 mm and 18 FR corresponds to a catheter with an outer diameter of 6 mm.

In one embodiment, the urinary catheter is a telescopic catheter.

In embodiments, the first closure is attached to the outer package by a first attachment and/or the second closure is attached to the outer package by a second attachment.

In embodiments, the first closure is attached to a proximal end of the outer package and the second closure is attached to a distal end of the package.

In one embodiment, this provides for a catheter assembly that is opened and the catheter removed from the outer package, with the second closure oriented away from ground and the first closure oriented towards ground, i.e. in an upright position with the second closure pointing upwards. Accordingly, when the outer package is opened and the second closure is thereby also opened, any liquid residing in the enclosure is pulled towards ground and prevented from exiting the enclosure. In one embodiment, this prevents, or decreases the chance of, liquid spilling onto a user opening the package. Also, in one embodiment, when the catheter is removed from the outer package and the first closure is opened, any liquid residing in the enclosure will be retained in the outer package. In embodiments, this prevents, or decreases the chance of, liquid spilling onto a user while removing the catheter from the outer package.

In embodiments, the first closure defines a first opening force and the second closure defines a second opening force, wherein the first opening force is greater than the second opening force. This may further improve the reliability of opening the outer package and removing the catheter from the outer package. Accordingly, if a pull from a second attachment along a second direction pulls the second closure open, and a pull from a first attachment along a first direction pulls the first closure open, it may be ensured that the second closure is opened before the first closure, even if the first direction is oriented opposite to the second direction. Moreover, if the catheter is held in place in the outer package by the first closure and opening the outer package creates a pull in the catheter through the second closure, configuring the second opening force to be greater than the first opening force, ensures that the second closure is opened before the first closure. Accordingly, the second closure is opened as the outer package is opened and the first closure is opened as the catheter and sleeve is removed from the outer package.

In embodiments, the sleeve is attached to a handle in the proximal end and/or the sleeve is attached to the connector in the distal, and the handle is configured to allow gripping of the catheter in the proximal end without touching the sleeve.

The handle may provide convenient means for the user to grab the catheter and improve the convenience of handling the catheter assembly and/or reduce the risk of contamination in relation to catheterization. In one embodiment, the first closure is configured to close a proximal opening of the handle and the second closure is configured to close the distal opening of the connector. In this case, opening the outer package and removing the catheter with the distal end pointing upwards may cause any liquid stored in the enclosure to be drained into the outer package. This may be a particularly intuitive orientation of the outer package to open it, which may add to the convenience of operating the catheter assembly.

In one embodiment, the sleeve is attached to the handle in such a manner that at least part of the handle is not covered by the sleeve, allowing the user to grab the handle without touching the sleeve. This may add to the convenience of the user. In one embodiment, the sleeve is attached to the connector in such a manner that at least part of the connector is not covered by the sleeve, allowing the user to grab the connector without touching the sleeve.

In embodiments, the handle defines a proximal opening, wherein the first closure comprises a proximal foil and a peelable weld, the peelable weld being arranged between the proximal foil and the proximal opening of the handle. By closing the handle by the first closure comprising the proximal foil and a peelable welding, the first closure may be opened by peeling open the peelable weld. In embodiments, the first closure including the proximal foil is attached to the outer package. This has the effect that following removal of the catheter from the outer package, little or no sign of the first closure is left. Also, the reliability of the first closure may be increased when configured according to present embodiments.

In embodiments, a proximal foil of the first closure comprises an extension extending beyond a proximal opening of a handle, wherein the first attachment comprises a weld between the extension of the proximal foil and the outer package. This is a simple way of constructing the first closure and attaching it to the outer package. The simplicity of the attachment may add to the reliability of the attachment. Present embodiments are particularly advantageous if the outer package comprises a foil.

In embodiments, the sleeve defines a proximal perimeter, wherein the first closure comprises a proximal foil and a peelable weld, the peelable weld being arranged between the proximal foil and the proximal perimeter of the sleeve. This allows a simple configuration of the first closure even if the catheter assembly does not comprise a handle. In one embodiment, the simplicity of the first closure improves the reliability of the first closure.

In embodiments, a proximal foil comprises an extension extending beyond a proximal perimeter of the sleeve, wherein a first attachment comprises a weld between the extension of the proximal foil and the outer package. This is a simple way of constructing the first closure and attaching it to the outer package. The simplicity of the attachment may add to the reliability of the attachment. Present embodiments are particularly advantageous if the outer package comprises a foil as it may make the joint fabrication of the outer package and the first closure more compatible. This in turn may improve the reliability of the first closure and first attachment. Also, if the proximal foil is attached to the outer package, the proximal foil may be left in the outer package after the catheter is removed from the outer package adding to the convenience of the user in relation to catheterization.

In embodiments, a handle defines a proximal opening, and the first closure comprises a proximal plug, the proximal plug being configured to detachably close the proximal opening of the handle, and wherein a first attachment attaches the proximal plug to the outer package. The proximal plug allows for simple yet effective configuration of the first closure. The proximal plug is attached to the outer package by the first attachment. The plug may be held in place by friction between the plug and the handle. In one embodiment, the plug is held in place by a peelable weld or an adhesive. In present context, a plug is meant as a substantially rigid structure configured to extend into the proximal opening when closed, and to be opened by pulling the plug out of the proximal opening. Present embodiments are particularly advantageous if the outer package comprises a substantially rigid structure such as a substantially rigid hollow tube, as it may make the joint fabrication of the outer package and the first closure more compatible. This in turn may improve the reliability of the first closure and first attachment.

In embodiments, the first closure comprises a rupturable zone of the sleeve, wherein a first attachment attaches the proximal end of the sleeve to the outer package. In this case, the sleeve may be arranged to enclose the proximal end of the catheter. This is a simple yet effective way of configuring the first closure. Accordingly, the reliability of the first closure may be improved, adding to the convenience of the user in relation to catheterization.

In embodiments, a distal end of the sleeve defines a perimeter, wherein the second closure comprises a distal foil, the distal foil being peelably welded to the distal opening of the connector and/or a distal perimeter of the sleeve. By closing the connector by the second closure comprising the distal foil and a peelable weld, the second closure may be opened by peeling open the peelable weld. In this case, the distal perimeter of the sleeve may advantageously be attached to the connector in such a manner that the connector is exposed allowing the user to grab the connector in a convenient manner.

In case the distal perimeter of the sleeve is closed by the second closure, the sleeve is allowed to be arranged so that it is attached to the connector and extends beyond the attachment between the sleeve and the connector. This may be a simple and reliably way of configuring the second attachment adding to the convenience of the user.

In embodiments, a distal foil comprises an extension extending beyond the distal opening of the connector and/or a distal perimeter of the sleeve, wherein a second attachment comprises a weld between the extension of the distal foil and the outer package. This is a simple way of constructing the second closure and attaching it to the outer package. The simplicity of the attachment may add to the reliability of the attachment. Present embodiments are particularly advantageous if the outer package comprises a foil as it may make the joint fabrication of the outer package and the second closure more compatible. This in turn may improve the reliability of the second closure and second attachment. This may further add to the convenience of handling the catheter, as the part of the second closure including the distal foil may then be attached to the outer package, and leave little or no sign of the second closure after the outer package has been opened.

In embodiments, the sleeve encloses the connector at a distal end of the sleeve, wherein the second closure comprises a rupturable zone of the sleeve, and a second attachment attaches the distal end of the sleeve to the outer package. In this case, the sleeve may be arranged to enclose the distal end of the catheter and the connector. This is a simple yet effective way of configuring the second closure. Accordingly, the reliability of the second closure may be improved, adding to the convenience of the user in relation to catheterization.

In embodiments, the second closure comprises a distal plug, the distal plug being configured to detachably close the distal opening of the connector, and a second attachment attaches the distal plug to the outer package. The distal plug allows for simple yet effective configuration of the second closure. The distal plug is attached to the outer package by the second attachment. The plug may be held in place by friction between the plug and the connector. The plug may also be held in place by a peelable weld or an adhesive. Present embodiments are particularly advantageous if the outer package comprises a substantially rigid structure such as a substantially rigid hollow tube, as it may make the joint fabrication of the outer package and the second closure more compatible. This in turn may improve the reliability of the second closure and second attachment.

In embodiments, the catheter assembly further comprises a liquid absorbing material arranged between the sleeve and the outer package. In one embodiment, the liquid absorbing material further decreases the chance that any liquid residing in the enclosure spills on the user in relation to opening the outer package and/or removing the catheter from the outer package. In one embodiment, the liquid absorbing material is arranged along part of the catheter. In one embodiment, it is arranged along the entire length of the catheter. It may preferentially be arranged near the place where the outer package is configured to be opened. The liquid absorbing material may also absorb liquid possibly residing on the outer surface of the sleeve, further increasing the chance that the outer surface of the sleeve of the removed catheter is dry to the touch. In one embodiment, the liquid absorbing material is made of open celled polyurethane foam with a PPI value between 20 and 100.

FIG. 1 illustrates a schematic cross-sectional view of an embodiment of a catheter assembly 1 with an intermittent urinary catheter 3 arranged inside an outer package 5. In embodiments, the catheter 3 includes a proximal insertion end 7, a distal connection end 9 and a connector 11 at the distal end 9. The catheter assembly 1 further includes a sleeve 13 of liquid impermeable material. The sleeve 13 is configured to define part of an enclosure 15 enclosing an insertable part of the catheter 3.

The catheter 3 includes a main tubular part 17 extending from the distal end 9 to the proximal end 7. In embodiments, a tip 19 is positioned in the proximal end 7 of the catheter 3 and is provided as a rounded closed end of the tube constituting the main part of the catheter 3. The tip 19 includes a set of eyelets 20 for allowing urine to enter the catheter 3. The catheter 3 includes the connector 11 in the distal end 9. In one embodiment, the connector 11 includes a flared end 21 so that the diameter of the connector 11 increases with respect to the tubular part 17. In one embodiment, the catheter 3 includes a handle 23 in the proximal end 9, which has a length allowing the user to manipulate the catheter 3.

In the embodiment of FIG. 1, the enclosure 15 encloses an amount of liquid acting as a swelling medium for activating the hydrophilic surface coating of the catheter 3. In one embodiment, the activating medium is a water based substance, such as sterile water, saline-solution, or any water based liquid. The enclosure 15 is closed by a first closure 25 in the proximal end 7 and closed by a second closure 27 in the distal end 9. In one embodiment, the first closure is attached to the outer package by a first attachment 26 and the second closure is attached to the outer package by a second attachment 28. The second closure 27 is configured to be opened as the outer package 5 is opened. The first closure 25 is configured to be opened as the catheter 3 and sleeve 13 is removed from the outer package 5.

In the embodiment of FIG. 1, the proximal end of the sleeve 13 is attached to a handle 23 by a third attachment 31, and the distal end of the sleeve 13 is attached to the connector 11 by a fourth attachment 33. The arrangement of the third and fourth attachments 31, 33 illustrated in FIG. 1 allows a user to grab the handle 23 and the connector 11 without touching the sleeve 13. In one embodiment, the third and fourth attachments 31, 33 are arranged in a liquid tight manner. By 'liquid tight manner' is meant that the attachments are done so that the liquid contained inside the enclosure 15 is prevented from exiting the enclosure 15 through the attachments 31, 33. This may be achieved e.g. by welding the sleeve 13 to the handle 23 and the connector 11.

In the embodiment illustrated in FIG. 1, the handle 13 includes a proximal opening 35. This proximal opening 35 is closed by the first closure 25. In one embodiment, the first closure 25 includes a proximal foil 37 and a peelable weld between the proximal foil 37 and the proximal opening 35. In one embodiment, the second closure 27 includes a distal foil 39 and a peelable weld between the distal foil 39 and the connector 11. In the embodiment of FIG. 1, a first extension 41 of the proximal foil 37 is welded to the outer package 5.

In the embodiment of FIG. 1, the distal foil 39 includes a second extension 47 extending beyond the distal opening 29 of the connector 11. The second extension 47 is attached to the outer package 5 by a second attachment 28 in the form of a weld 49. In one embodiment, the outer package 5 is a foil package, which is opened by peeling open a peelable weld 51. A user peeling open the peelable weld 51 then continues to pull the foils apart to fully open the outer package 5 and to open the second closure 27. A schematic of an opened outer package 5 with an opened second closure 27 is illustrated in FIG. 2.

In the embodiment of FIG. 1, the outer package 5 is opened near the connector 11. The second closure 27 closing the distal opening 29 of the connector 11 is opened as a user opens the outer package 5. The user then grabs the connector 11 and pulls the catheter 3 and sleeve 13 out of the outer package 5. This opens the first closure 25 and the liquid residing in the enclosure 15 is drained through the opened first closure 25 and the eyelets 20 into the outer package 5.

Figure 2:
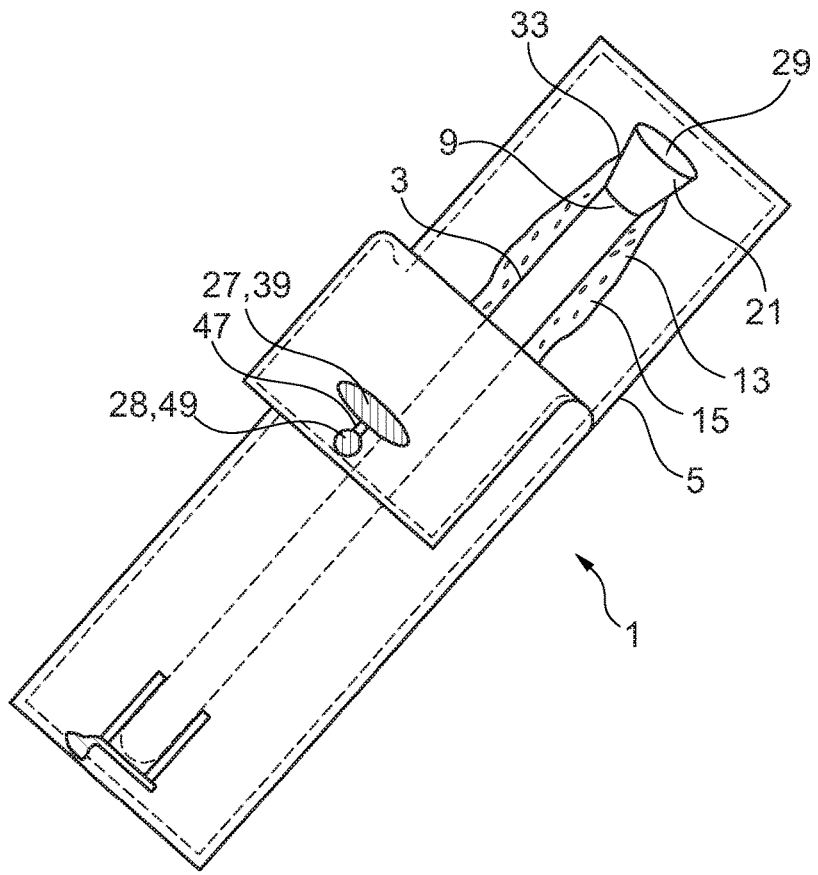
FIG. 2 illustrates an embodiment of a catheter assembly.

FIG. 2 illustrates an embodiment of a catheter assembly 1. In the embodiment of FIG. 2, the outer package 5 has been opened whereby the second closure 27 has also been opened. In this case, air is allowed access to the enclosure 15 through the distal opening 29 of the connector 11. In one embodiment, when the catheter 3 is removed from the outer package 5 and the first closure 25 is opened, the liquid in the enclosure 15 is drained into the outer package 5 through the opened first closure 25 and the eyelets 20.

Figure 3:
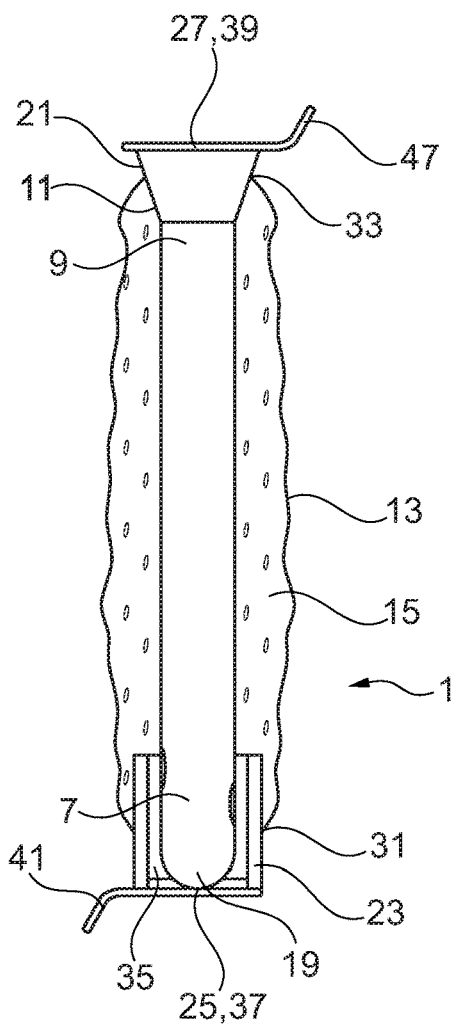
FIG. 3 illustrates a schematic cross-sectional side view of an embodiment of a catheter assembly.

FIG. 3 illustrates the same catheter assembly 1 as illustrated in FIG. 1. However, in FIG. 3 the catheter assembly 1 is illustrated without the outer package 5 in order to more clearly illustrate the remaining parts of the catheter assembly 1.

Figure 4:
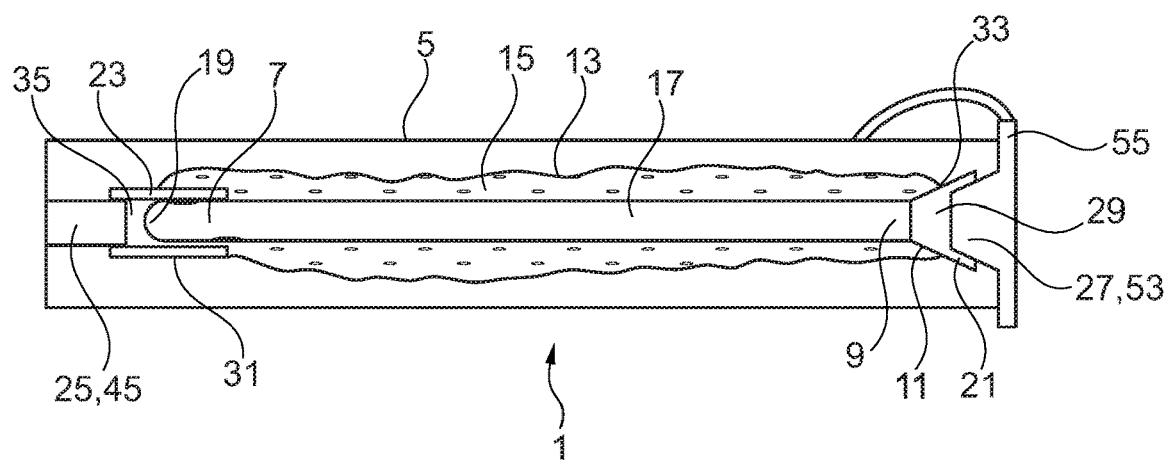
FIG. 4 illustrates a schematic cross-sectional side view of an embodiment of a catheter assembly.

FIG. 4 illustrates an embodiment of a catheter assembly 1. In this embodiment, the first closure 25 includes a proximal plug 45. The proximal plug 45 is arranged to extend into the proximal opening 35 of the handle 23 and is thereby held in place by friction between the proximal plug 45 and the handle 23. In the embodiment of FIG. 4, a weld between the proximal plug 45 and the outer package 5 attaches the proximal tube 45 to the outer package 5. In one embodiment, the outer package 5 is a substantially rigid hollow tube.

Figure 5:
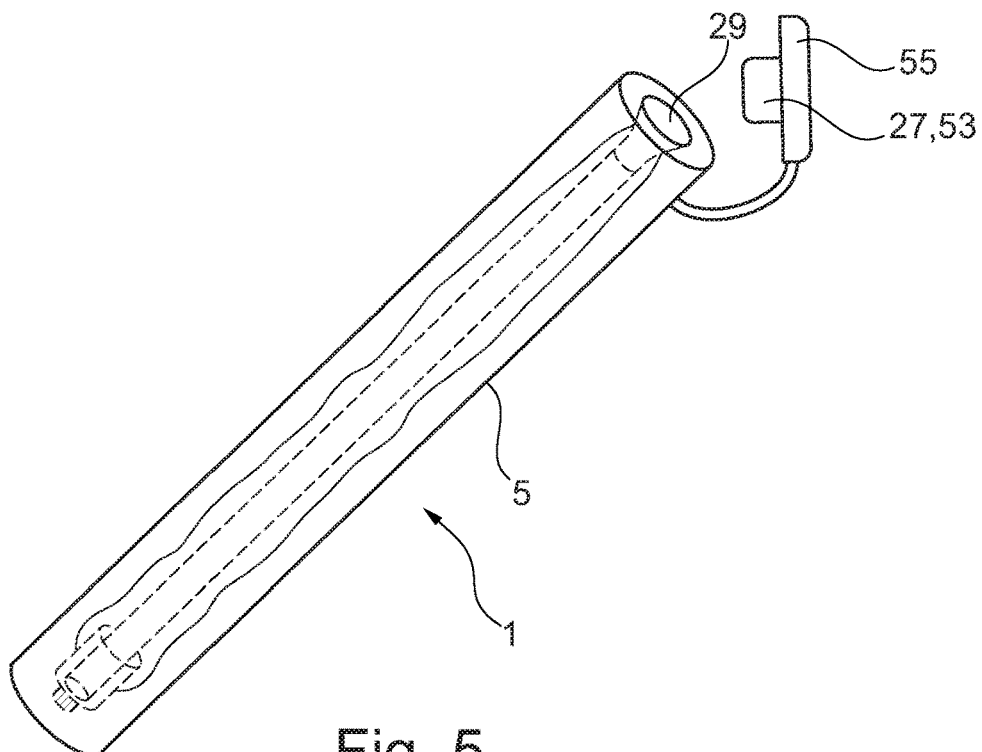
FIG. 5 illustrates an embodiment of a catheter assembly.

In the embodiment of FIG. 4, the second closure 27 includes a distal plug 53. The distal plug 53 extends into the distal opening 29 of the connector 11. The distal plug 53 is held in place by friction between the distal plug 53 and the connector 11. In this way, the distal plug 53 detachably closes the distal opening 29 of the connector 11. In the embodiment of FIG. 4, the distal plug 53 is integrally formed with a lid 55 of the outer package 5. A user opening the lid 55 is then also removing the distal plug 53 from the connector 11 and thereby opening the second closure 27. FIG. 5 illustrates such an opened catheter assembly 1. In one embodiment, the outer package 5 is a substantially rigid hollow tube. Then, as the user pulls the catheter 3 and sleeve 13 out of the outer package 5, the liquid residing in the enclosure 15 is drained into the outer package 5 through the opened first closure 25 and the eyelets 20.

Figure 6:
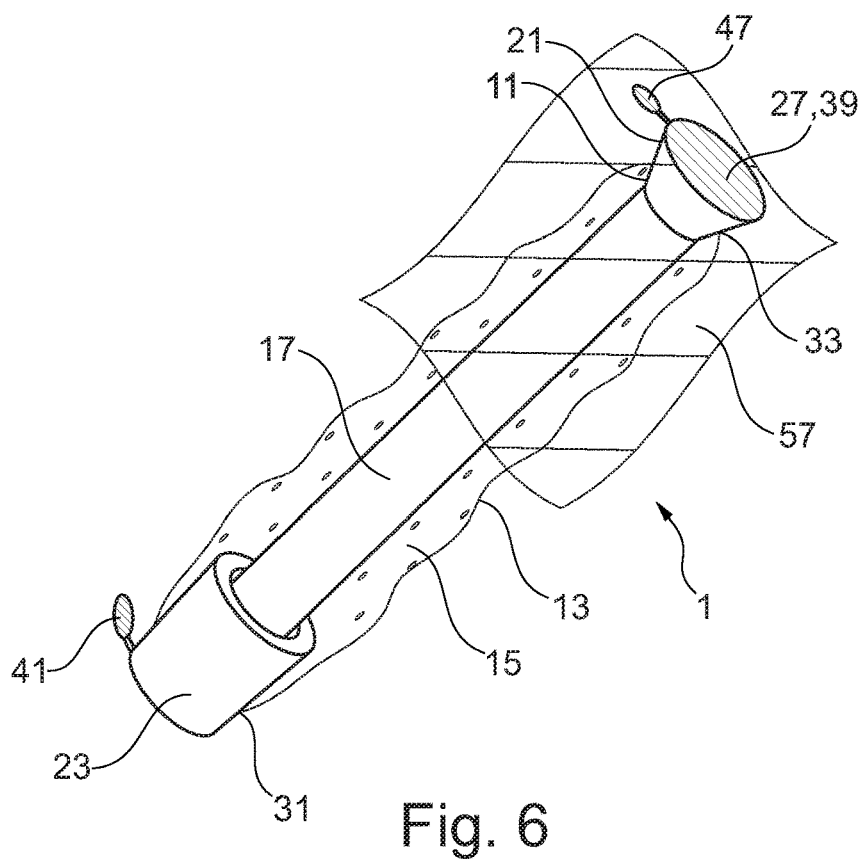
FIG. 6 illustrates an embodiment of a catheter assembly.

FIG. 6 illustrates an embodiment of a catheter assembly 1, in which the outer package 5 is hidden in order to more clearly illustrate the remaining parts of the catheter assembly 1. In the embodiment of FIG. 6, a liquid absorbing material 57 is arranged near the distal opening 29 of the connector 11. In one embodiment, the distal opening 29 of the connector 11 is arranged near the place where the outer package 5 is configured to be opened.

The invention claimed is:

1. A urinary catheter assembly comprising:
   a closed package;
   a urinary catheter sealed inside of the closed package, the urinary catheter comprising:
      a tubular portion extending from a proximal end adapted for insertion into a urethra to a distal end,
      a connector coupled to the distal end of the tubular portion, where the connector defines a distal opening of the urinary catheter,
      a hydrophilic coating applied to the tubular portion,
      a handle disposed around the proximal end of the tubular portion, where the handle defines a proximal opening adapted to allow passage of the proximal end of the tubular portion out through the handle,
      a sleeve enclosing and extending over the tubular portion, with a first part of the sleeve attached to the handle and a second part of the sleeve attached to the connector,
      a first closure sealing the proximal opening of the handle and including a first extension portion that is coupled to the closed package,
      a second closure sealing the distal opening of the connector and including a second extension portion coupled to the closed package; and
   a liquid contained inside the sleeve and adapted to wet the hydrophilic coating.

2. The urinary catheter assembly of claim 1, wherein the urinary catheter is an intermittent urinary catheter.

3. The urinary catheter assembly of claim 1, wherein the first closure and the second closure combine to provide a liquid tight seal for the liquid contained inside the sleeve.

4. The urinary catheter assembly of claim 1, wherein, when the closed package is opened, the second extension portion is adapted to remove the second closure from the distal opening of the connector.

5. The urinary catheter assembly of claim 1, wherein, when the urinary catheter is removed from the package, the first extension portion is adapted to retain the first closure inside the package and open the proximal opening of the handle to allow the liquid contained inside the sleeve to drain out of the sleeve and into the package.

6. The urinary catheter assembly of claim 1, wherein the closed package comprises a water vapour impermeable material.

7. The urinary catheter assembly of claim 1, wherein the closed package comprises a gas-impermeable material.

8. The urinary catheter assembly of claim 1, wherein the closed package comprises an aluminum water vapour impermeable material.

9. The urinary catheter assembly of claim 1, wherein the sleeve is collapsible toward the connector as the proximal end of the tubular portion is extended out of the proximal opening in the handle.

10. The urinary catheter assembly of claim 1, wherein the sleeve is liquid impermeable.

11. The urinary catheter assembly of claim 1, wherein the urinary catheter is a telescopic catheter.

12. The urinary catheter assembly of claim 1, wherein the first part of the sleeve is connected to the handle such that a section of the handle is not covered by the sleeve allowing the user to touch the handle without touching the sleeve.

13. The urinary catheter assembly of claim 1, wherein the sleeve and the handle are adapted to slide toward the connector and relative to the tubular portion.

* * * * *